United States Patent [19]

Scholte

[11] Patent Number: 4,720,598
[45] Date of Patent: Jan. 19, 1988

[54] PROCESS FOR PREPARING A BASIC LITHIUM PHOSPHATE CATALYST FOR THE ISOMERIZATION OF ALKENE OXIDES

[75] Inventor: Hubertus B. Scholte, Sittard, Netherlands

[73] Assignee: Stamicarbon B.V., Netherlands

[21] Appl. No.: 878,507

[22] Filed: Jun. 23, 1986

Related U.S. Application Data

[62] Division of Ser. No. 795,643, Nov. 6, 1985, abandoned.

[30] Foreign Application Priority Data

Nov. 28, 1984 [NL] Netherlands ......................... 8403616

[51] Int. Cl.$^4$ .............................................. C07C 29/56
[52] U.S. Cl. .................................... 568/908; 423/312; 423/313; 502/208
[58] Field of Search .......................................... 568/908

[56] References Cited

U.S. PATENT DOCUMENTS

| | | | |
|---|---|---|---|
| 2,426,264 | 8/1947 | Fowler et al. | 568/908 |
| 2,826,622 | 3/1958 | Kemp | 502/208 X |
| 2,986,585 | 5/1961 | Denton | 568/908 |
| 3,040,815 | 6/1962 | Pamtello | 169/57 |
| 3,040,816 | 6/1962 | Slough | 169/9 |
| 3,044,850 | 7/1962 | Denton | 423/313 |
| 3,122,588 | 2/1964 | Phillips et al. | 502/208 |
| 3,210,338 | 10/1965 | Huber et al. | 502/208 X |
| 3,238,264 | 3/1966 | Rowton | 568/908 |
| 3,274,121 | 9/1966 | Schneider | 568/908 |
| 3,325,245 | 6/1967 | Rowton | 423/312 |
| 4,065,510 | 12/1977 | Schreyer et al. | 502/208 X |
| 4,342,666 | 8/1982 | Hardy | 502/208 |
| 4,481,361 | 11/1984 | Denkel et al. | 502/208 X |

FOREIGN PATENT DOCUMENTS

| | | | |
|---|---|---|---|
| 1271082 | 6/1968 | Fed. Rep. of Germany | 502/208 |
| 0902953 | 8/1962 | United Kingdom | 502/208 |
| 1057137 | 2/1967 | United Kingdom | 502/208 |
| 1242135 | 8/1971 | United Kingdom | 502/208 |

*Primary Examiner*—J. E. Evans
*Attorney, Agent, or Firm*—Cushman, Darby & Cushman

[57] ABSTRACT

Process for preparing a basic lithium phosphate catalyst suitable for the gas phase isomerization of an alkene oxide to the corresponding alcohol, in which process an aqueous solution of a lithium compound is mixed in the presence of an alkali metal hydroxide with an aqueous solution of a phosphate salt or phosphoric acid, the process being characterized in that the aqueous solution of the phosphate salt or phosphoric acid is added evenly during a period of at least six hours to the homogeneously stirred aqueous solution of the lithium compound, upon which the precipitated lithium phosphate is washed with water and subsequently calcined.

7 Claims, No Drawings

PROCESS FOR PREPARING A BASIC LITHIUM PHOSPHATE CATALYST FOR THE ISOMERIZATION OF ALKENE OXIDES

This is a division of application Ser. No. 795,643 filed Nov. 6, 1985, which was abandoned upon one filing hereof.

The invention relates to a process for preparing a basic lithium phosphate catalyst suitable for the gas phase isomerization of an alkene oxide to the corresponding alcohol, in which process an aqueous solution of a lithium compound is mixed in the presence of an alkali metal hydroxide with an aqueous solution of a phosphate salt or phosphoric acid.

Such a process is known from U.S. Pat. No. 2,986,585 and DE-A-1,271,082.

The invention also relates to a process for the gas phase isomerization of an alkene oxide to the corresponding alcohol by means of a basic lithium phosphate catalyst.

From U.S. Pat. No. 2,986,585 it is known that a catalyst prepared according to that process shows a steady deactivation when used in the process for the isomerization of alkene oxides, for which reason it is necessary for the catalyst to be periodically regenerated. In U.S. Pat. No. 3,040,815 and U.S. Pat. No. 3,040,816 strong deactivation is reported within a process period of 24–48 hours, upon which regeneration is necessary. In DE-A-1,271,082 it is indicated that the deactivation may be avoided to a large extent by washing the precipitated lithium phosphate moisture-free with a water-miscible organic liquid during the preparation of the catalyst.

The object of the invention is to provide a process for preparing a basic lithium phosphate catalyst that does not show such deactivation, in which process, moreover, no organic auxiliaries are used to prevent deactivation.

According to the invention a process for preparing a basic lithium phosphate catalyst suitable for the gas phase isomerization of an alkene oxide to the corresponding alcohol, in which process an aqueous solution of a lithium compound is mixed in the presence of an alkali metal hydroxide with an aqueous solution of a phosphate salt or phosphoric acid, is characterized in that the aqueous solution of the phosphate salt or phosphoric acid is added evenly during a period of at least six hours to a homogeneously stirred aqueous solution of the lithium compound, upon which the precipitated basic lithium phosphate is washed with water and subsequently calcined.

In applying the process according to the invention, to be called the injection-precipitation process, it has been found that a weakly acid, strongly basic, bifunctional catalyst is obtained showing a very good stability in the gas phase isomerization of an alkene oxide to the corresponding alcohol. In addition, it has been found that the catalyst thus obtained shows a strongly increased activity (expressed in g alcohol per liter catalyst and per hour) in respect of that of the known state of the art.

In respect of the isomerization of an alkene oxide to the corresponding alcohol, two process varieties are known both proceeding from the use of a basic lithium phosphate as a catalyst, viz. a slurry phase process and a gas phase process.

From U.S. Pat. No. 3,238,264 as well as from GB-A-969,344 it may be learned that the problems with the gas phase isomerization are so great (inter alia the said rapid deactivation of the catalyst) that preference is given to a slurry phase process, with all the disadvantages that go with it (such as slurry separation problems). From U.S. Pat. No. 3,238,264 as well as from U.S. Pat. No. 3,325,245 it is known that for the preparation of a suitable slurry phase lithium phosphate catalyst it is desirable for the components to be added to each other quickly, because slow metering will result in a lower activity and productivity.

Surprisingly it has now been found that in the preparation of a catalyst for the gas phase isomerization of an alkene oxide the metering of the aqueous solution of the phosphate salt or the phosphoric acid to a homogeneously stirred aqueous solution of a lithium compound must in contrast be very slow and even. Rapid metering produces a less active catalyst, which becomes deactivated, too.

For the preparation of the catalyst the lithium compound started from its advantageously LiOH and the phosphate-supplying compound advantageously phosphoric acid.

The alkali metal hydroxide to be used in the preparation of the catalyst may, as indicated in for instance U.S. Pat. No. 2,986,585, be taken from the group of lithium, sodium or potassium hydroxide, while mixtures of these may be applied also.

In order to give the basic lithium phosphate optimum catalytic properties, the basic lithium phosphate precipitated during the preparation process should advantageously subsequently be washed with water for such a length of time that the pH of the washing water is constant.

In addition to applying the bifunctional lithium phosphate as such, this lithium phosphates may also well be mixed with additives or supporting materials, such as asbestos, talcum, activated carbon, silica and $\alpha$-alumina. Of these $\alpha$-alumina is to be preferred.

The basic lithium phosphate prepared to the invention shows an isomerization activity exceeding the values mentioned in this respect in the state of the art; in this connection U.S. Pat. No. 2,986,595 mentions activities of 250–550 g alcohol per liter catalyst and per hour. With a catalyst according to the invention activities of 600–1200 g alcohol per liter catalyst and per hour are not exceptional. In analyzing the catalyst resulting from the process according to the invention it has been found that, compared with the known catalysts from the state of the art, they have a large BET surface: approx. 125 $m^2$ per gramme lithium phosphate; the BET surfaces of basic lithium phosphate reported in literature range from 30 to 50 $m^2/g$ (e.g. P. Desmarescaux in: Inf. Chim. 74, 27–31 (1969)). The increased activity of the catalysts according to the invention may therefore well be attributable to the higher BET surface.

If a catalyst prepared according to the invention is treated with a steam/air mixture after calcination, an improvement of the activity of this catalyst is obtained compared with a catalyst not treated with such a mixture.

The catalyst obtained according to the invention is highly suitable for the gas phase isomerization of an alkene oxide to the corresponding alcohol and is particularly suitable for the isomerization of propylene oxide (1,2-epoxypropane) to allyl alcohol (2-propenol). Such gas phase isomerizations usually take place at temperatures between 250° and 350° C. The choice of the reaction temperature is determined on the one side by the activity (which of course increases as the temperature increases) and on the other by the selectivity to the desired alcohol. The catalyst has been found particularly insensitive to deactivation at temperatures above 290° C. That is why preference is given to using the catalyst obtained according to the invention in the temperature range of 290°-235° C.

The pressure at which the isomerization is carried out is not critical. Besides carrying out the process under the atmospheric conditions generally applied, it is possible to use reduced or elevated pressure, e.g. between 0.01 and 1 MPa, although care should then preferably be taken that during the isomerization the temperature is such that in the process there will be no capillary condensation of feedstock and/or product, which may have an adverse effect on the catalytic properties.

The invention will be further elucidated by means of the following non-restrictive examples.

EXAMPLE I

A. Catalyst Preparation 95.8 g LiOH (4 moles) is dissolved in 1 l $H_2O$ while being firmly stirred and heated to 40°-50° C. The aqueous LiOH solution (pH=14.0) is injected below the liquid level, via a capillary, with a solution of 98 g $H_3PO_4$ (1 mole) in 1 l $H_2O$ at a rate of 80 cm$^3$/h using a peristaltic pump.

After complete addition of the solution and formation of a very fine white precipitate the pH of the supernatant liquid falls to 12.4. After centrifugation and drying in a drying oven at about 90° C., the specific surface is determined: $S_{BET}$=125 m$^2$/g (after 3 h calcining at 300° C.).

Subsequently, 61.3 grammes of this dried, basic lithium phosphate and 18.4 g $\alpha$-alumina K1, Dr. Otto (100 $\mu$m$\leq$d$\leq$200 $\mu$m, $S_{BET}$=1.5 m$^2$/g), are suspended in 2 l water in a beaker and firmly stirred at about 70°-80° C. for 2-3 hours.

After precipitation the pH of the supernatant liquid has decreased to 11.7. The homogeneously stirred liquid is centrifuged off and the filter cake is subsequently washed with water five times, so that a constant pH (10.8) of the washing liquid is obtained. After that the filter cake is dried, for ease of handling, in a drying oven at 80° C. for about 1-2 hours.

After pre-drying in the drying oven, the filter cake is pounded in a mortar and subsequently calcined at about 300° C. for about 16 h. The powder is subsequently pressed into cylindrical pellets, length 2 mm and diameter 5 mm. The specific surface is: $S_{BET}$=41 m$^2$/g.

B. Isomerization of Propylene Oxide

The above catalyst is used for the gas phase isomerization of propylene oxide to allyl alcohol in a fixed bed, Pyrex glass tubular reactor, filled with 4.5 g catalyst, under atmospheric conditions at a temperature of 305°-310° C. The reactor is heated by means of an electrically heated carborundum fluid bed. Propylene oxide is metered in gaseous form from a saturator provided with a thermostat and filled with propylene oxide, through which anhydrous and oxygen-free helium is passed. By using ceramic packing in the saturator a degree of saturation of 93.5% is achieved. Before reaching the catalyst bed the feed is pre-heated in the reactor by first passing it through a bed of quartz splinters of a few centimeters' height.

The exhaust gas from the reactor is cooled to −43° C., the non-condensable part being subjected on-line and the condensable part being subjected off-line to a GLC analysis. The non-condensable reactor exhaust gas substantially consists of helium and a trace of propylene oxide.

After an initial drop in activity, a stabilization of the activity sets in.

The effect of the propylene oxide load on this stabilized activity and on the selectivity is determined, see table I.

TABLE I

| WHSV* $(h^{-1})$ | Conversion (%) | Selectivity (%) | Productivity | |
|---|---|---|---|---|
| | | | a | b |
| 1.18 | 57 | 89 | 0.60 | 692 |
| 2.44 | 46 | 88 | 0.99 | 1142 |
| 3.13 | 30 | 86 | 0.81 | 934 |

*Weight hourly space velocity (grammes feed per hour per gramme lithium phosphate);
$^a$productivity expressed in grammes allyl alcohol per gramme lithium phosphate and per hour;
$^b$productivity expressed in grammes allyl alcohol per liter catalyst and per hour (bulk density 1500 g/l).

These experiments cover a period of 450 hours in all in which no deactivation whatsoever occurs.

Comparative Example A

With a catalyst prepared as in example 1 an isomerization experiment is performed at a temperature of 255°-260° C. under conditions otherwise analogous to those of example 1.

Initially the conversion is 29% at a WHSV of 3.02 h$^{-1}$; it falls in about 30 hours to 15%, the selectivity remains the same at about 80%.

By means of a regeneration process an effort is made to reactivate the catalyst. The procedure followed in this reactivation is as follows. Water is mixed with air in an evaporator at about 230° C. and passed over the catalyst to be regenerated. At first the temperature of the catalyst bed is about 200° C. and via a gradual heating-up at a heating rate of $\beta$=1° C./min the temperature is raised to 360° C. This temperature is maintained for 2 hours.

A regeneration process with such a steam/air mixture (GHSV* total (=liters feed per hour and per liter catalyst)=2843 h$^{-1}$; 8% (vol) $O_2$; 64% (vol) $H_2O$) has a distinct positive effect on the deactivated catalyst described above:—after the regeneration process the greyish brown colour of the lithium phosphate catalyst changed into the original white—at the temperature of 255°-260° C. the catalytic activity of the deactivated catalyst has been restored and has in fact even been improved: the selectivity for allyl alcohol increases by about 4% to about 84% and the total degree of conversion, reduced to the initial level of about 29%, now shows a slightly slower decline during time: a complete drop of the total degree of conversion to a level of 0% now takes at least approx. 80 hours; a stabilization of the activity, however, is not obtained.

EXAMPLE II

At 305°-310° C. after having been subjected to a regeneration process with steam/air as described in the preceding comparative example, a catalyst consisting of 76.9% (wt) lithium phosphate/23.1% (wt) $\alpha$-alumina, prepared as in example I, which catalyst has become deactivated by its operation at 225°-260° C., shows catalytic properties the same as those of a fresh catalyst used in the gas phase isomerization of propylene oxide to alkyl alcohol at a temperature of 305°–310° C. as in example I.

At a WHSV of 2.8 h$^{-1}$ a stable conversion of about 40% is obtained for more than 80 hours; the selectivity for this period is about 88%.

EXAMPLE III

A catalyst consisting of 76.9% (wt) lithium phosphate/23.1% (wt) α-alumina, prepared as in example I, is subjected for 4 hours to a treatment with a steam/air mixture containing 5% (vol) O$_2$ and 75% (vol) H$_2$O at a temperature of approx. 250° C. with a GHSV of 4172 h$^{-1}$.

This catalyst is subsequently used for the gas phase isomerization of propylene oxide to allyl alcohol under the conditions of example I.

At a WHSV of 2.49 h$^{-1}$ the resulting conversion is 47% at a selectivity of 89% and an allyl alcohol yield of 1.04 grammes per gramme lithium phosphate and per hour, corresponding with 1200 grammes allyl alcohol per liter catalyst and per hour.

I claim:

1. A process for the gas phase isomerization of propylene oxide to allyl alcohol which comprises contacting propylene oxide at a temperature of from about 290° C. to about 325° C. with a fixed bed composed of a basic lithium phosphate catalyst prepared by evenly adding an aqueous solution of a phosphate salt or phosphoric acid during a period of at least 6 hours to a homogenously stirred aqueous solution of a lithium compound, on which the precipitated lithium phosphate is washed with water and subsequently calcined to form said catalyst, whereby said allyl alcohol is obtained by isomerization of said propylene oxide.

2. Process according to claim 1, wherein said lithium compound is LiOH.

3. Process according to claim 1, using phosphoric acid.

4. Process according to claim 1, wherein said precipitated lithium phosphate is washed with water for a length of time sufficient that the pH of the washing water is constant.

5. Process according to claim 4, wherein said basic lithium phosphate is mixed, after washing, with additives or supporting materials in the formation of said catalyst.

6. Process according to claim 5, wherein said basic lithium phosphate is mixed with α-alumina.

7. Process according to claim 4, wherein said basic lithium phosphate is treated, after calcining with a steam/air mixture.

* * * * *